US010709411B2

(12) United States Patent
Lee et al.

(10) Patent No.: US 10,709,411 B2
(45) Date of Patent: Jul. 14, 2020

(54) CALIBRATION DEVICE AND METHOD FOR CALIBRATING THREE-DIMENSIONAL IMAGING EQUIPMENT

(71) Applicant: ELECTRONICS AND TELECOMMUNICATIONS RESEARCH INSTITUTE, Daejeon (KR)

(72) Inventors: SooYeul Lee, Daejeon (KR); Jang Hwan Choi, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 315 days.

(21) Appl. No.: 15/871,503

(22) Filed: Jan. 15, 2018

(65) Prior Publication Data

US 2019/0021688 A1   Jan. 24, 2019

(30) Foreign Application Priority Data

Jul. 24, 2017 (KR) .................. 10-2017-0093772

(51) Int. Cl.
*A61B 6/00* (2006.01)
*A61B 6/02* (2006.01)
*A61B 90/00* (2016.01)

(52) U.S. Cl.
CPC .............. *A61B 6/583* (2013.01); *A61B 6/027* (2013.01); *A61B 90/39* (2016.02); *A61B 2090/3966* (2016.02); *G05B 2219/37008* (2013.01)

(58) Field of Classification Search
CPC ......... A61B 6/582; A61B 6/583; A61B 6/585; A61B 6/58; A61B 2090/392; A61B 2090/3966; A61B 2090/3983; A61B 6/027; A61B 90/39; G05B 2219/37008; G05B 2219/37014
See application file for complete search history.

(56) References Cited

U.S. PATENT DOCUMENTS

| | | | |
|---|---|---|---|
| 5,442,674 A | 8/1995 | Picard et al. | |
| 8,104,958 B2 | 1/2012 | Weiser et al. | |
| 8,666,133 B2 | 3/2014 | Vermandel et al. | |
| 2013/0003913 A1 | 1/2013 | Jeong et al. | |
| 2014/0369460 A1 | 12/2014 | Jeong et al. | |
| 2018/0014809 A1* | 1/2018 | Lin | A61B 6/4417 |

OTHER PUBLICATIONS

J. H. Siewerdsen et al., "Volume CT with a flat-panel detector on a mobile, isocentric C-arm: Pre-clinical investigation in guidance of minimally invasive surgery", Medical Physics, Jan. 2005, pp. 241-254, vol. 32, No. 1, Am. Assoc. Phys. Med.
Stefan Hoppe, "Accurate Cone-Beam Image Reconstruction in C-Arm Computed Tomography", Apr. 12, 2008, pp. 1-90.

* cited by examiner

*Primary Examiner* — Don K Wong

(57) ABSTRACT

Provided is a calibration device for three-dimensional imaging equipment including a first bead group including first beads arranged in a first pattern, and a second bead group including second beads arranged in a second pattern different from the first pattern, wherein the first and second bead groups have different cross ratios or different segment ratios from each other, the first beads are arranged in a line, and the second beads are arranged in a line.

8 Claims, 12 Drawing Sheets

CALIBRATION DEVICE AND METHOD FOR CALIBRATING THREE-DIMENSIONAL IMAGING EQUIPMENT

CROSS-REFERENCE TO RELATED APPLICATIONS

This U.S. non-provisional patent application claims priority under 35 U.S.C. § 119 of Korean Patent Application No. 10-2017-0093772, filed on Jul. 24, 2017, the entire contents of which are hereby incorporated by reference.

BACKGROUND

The present disclosure herein relates to a calibration device and method for calibrating a three-dimensional imaging equipment.

A three-dimensional imaging equipment may capture an image of an object while revolving in a predetermined circular orbit. When a gantry of the imaging equipment revolves in an accurate circular orbit, positional relationships among a source, a detector, and a subject may be briefly defined with several parameters (e.g. parameters such as a gantry rotation angle, a distance between the source and detector, a distance between a source and a rotation axis, and a detector rotation angle). When the parameters are accurate, a two-dimensional image detected by the detector may be easily reconstructed to a 3-dimensional image. However, since the gantry is large and heavy, it is not easy to make the gantry revolve in a perfectly circular orbit. For example, since a structural deflection or modification easily occurs, the positional relationships among the source, detector, and subject are not easily described with the gantry rotation angle and several parameters. Despite of occurrence of the structural deflection or modification, when the three-dimensional image is reconstructed with the gantry rotation angle and several parameters, an reconstructed image may be blurred.

However, even when positional relationships between an X-ray source, a detector, and a subject are not described precisely with a rotation angle and several parameters, when a rotational trajectory of the gantry is sufficiently repeatable, the imaging equipment may be simply, precisely, and geometrically calibrated.

SUMMARY

The present disclosure provides a device and method for calibrating three-dimensional imaging equipment.

However, the purpose of the invention is not limited to the above-described disclosure.

An embodiment of the inventive concept provides a calibration device for three-dimensional imaging equipment, including: a first bead group including first beads arranged in a first pattern; and a second bead group including second beads arranged in a second pattern different from the first pattern, wherein the first and second bead groups have different cross ratios or different segment ratios from each other, the first beads are arranged in a line, and the second beads are arranged in a line.

In an embodiment, the calibration device may further include a body having a polyhedron shape, wherein the body includes first and second side surfaces having a rectangular shape, and the first and second bead groups are respectively provided onto the first and second side surfaces.

In an embodiment, the first beads may be arranged in a first straight line direction from a first vertex of the first side surface towards a second vertex facing in a first diagonal direction, and the second beads may be arranged in a second straight line direction from a third vertex of the second side surface towards a fourth vertex facing in a second diagonal direction.

In an embodiment, the first beads may be at least four, and the second beads may be at least four.

In an embodiment, arrangement intervals between the first beads may be different from those between the second beads.

In an embodiment, the calibration device may further include a body having a polyhedron shape, wherein the body includes first and second side surfaces different from each other, and the first and second bead groups are provided onto the first and second side surfaces.

In an embodiment, each of the first and second side surfaces may be triangular.

In an embodiment, the first beads may be arranged in a first straight line direction from a first vertex of the first side surface towards a center of a side facing the first vertex, and the second beads may be arranged in a second straight line direction from a second vertex of the second side surface towards a center of a side facing the second vertex.

In an embodiment of the inventive concept, a calibration method for a three-dimensional imaging equipment includes: forming a projection image for a plurality of bead groups; determining a plurality of projection groups from the projection image; respectively mapping the plurality of projection groups to the plurality of bead groups; and obtaining a projection matrix on a basis of mapping information for the plurality of projection groups and the plurality of bead groups, wherein each of the plurality of bead groups includes a plurality of beads arranged in a line, and each of the plurality of projection groups includes a plurality of projection beads arranged in a line.

In an embodiment, the respective mapping of the plurality of projection groups to the plurality of bead groups may be performed using a segment ratio of each of the plurality of bead groups.

In an embodiment, the respective mapping of the plurality of projection groups to the plurality of bead groups may include: providing imaginary bead groups forming one of the plurality of projection groups; generating data about first segment ratios of the imaginary bead groups; generating data about second segment ratios of the plurality of bead groups; selecting one of the plurality of bead groups, a difference between the second segment ratio of the selected bead group and each of the first segment ratios being minimized; and mapping the selected bead group to the one of the plurality of projection groups, wherein each of the imaginary bead groups includes imaginary beads arranged in a line.

In an embodiment, the providing of the imaginary bead groups may include: providing an imaginary source unit; providing imaginary light paths connecting a plurality of projection beads included in the one of the plurality of projection groups to the imaginary source unit; providing imaginary bead lines passing the imaginary light paths; and disposing the imaginary beads at cross points of the imaginary light paths and each of the imaginary bead lines.

In an embodiment, the plurality of projection beads includes in the one of the plurality of projection groups may be connected to each other by a straight line, and the imaginary source unit may be provided to be separated from a center of the straight line in a perpendicular direction.

In an embodiment, the respective mapping of the plurality of projection groups to the plurality of bead groups may be performed using cross ratios of the plurality of bead groups and cross ratios of the plurality of projection groups.

In an embodiment, the respective mapping of the plurality of projection groups to the plurality of bead groups may include: generating data about the cross ratios of the plurality of projection groups; generating data about the cross ratios of the plurality of bead groups; and selecting a projection group and a bead group having a same cross ratio from among the plurality of projection groups and the plurality of bead groups.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
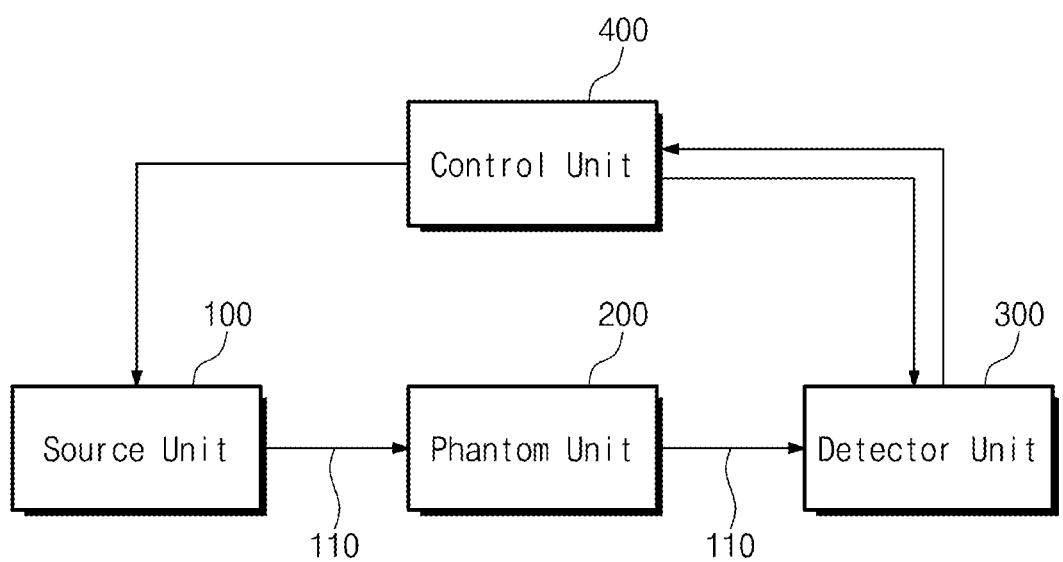
FIG. 1 is a block diagram of a calibration system of a three-dimensional imaging equipment.

The embodiments of the present invention will now be described with reference to the accompanying drawings for sufficient understanding of a configuration and effects of the inventive concept. However, the inventive concept is not limited to the following embodiments and may be embodied in different ways, and various modifications may be made thereto. The embodiments are just given to provide complete disclosure of the inventive concept and to provide thorough understanding of the inventive concept to those skilled in the art.

Like reference numerals refer to like elements throughout. Embodiments in the specification will be described with reference to cross-sectional views that are ideal exemplary views of the technical idea of the present invention. In the drawings, the thicknesses of layers and regions are exaggerated for clarity. Thus, the regions illustrated in the figures are schematic in nature and their shapes may be not intended to illustrate the actual shape of a region of a device and are not intended to limit the scope of example embodiments. It will be understood that although the terms "first", "second", etc. may be used herein to describe various components, these components should not be limited by these terms. The terms are used only for distinguishing a constituent element from other constituent elements. Exemplary embodiments described and illustrated here include complementary exemplary embodiments thereof.

The terms and words used in the following description and claims are to describe embodiments but are not limited the inventive concept. As used herein, the singular forms "a," "an" and "the" are intended to include the plural forms as well, unless the context clearly indicates otherwise. It will be further understood that the terms "comprises" and/or "comprising" used herein specify the presence of stated features or components, but do not preclude the presence or addition of one or more other features or components.

Hereinafter, the embodiments of the present invention will now be described in detail with reference to the accompanying drawings.

Figure 2:
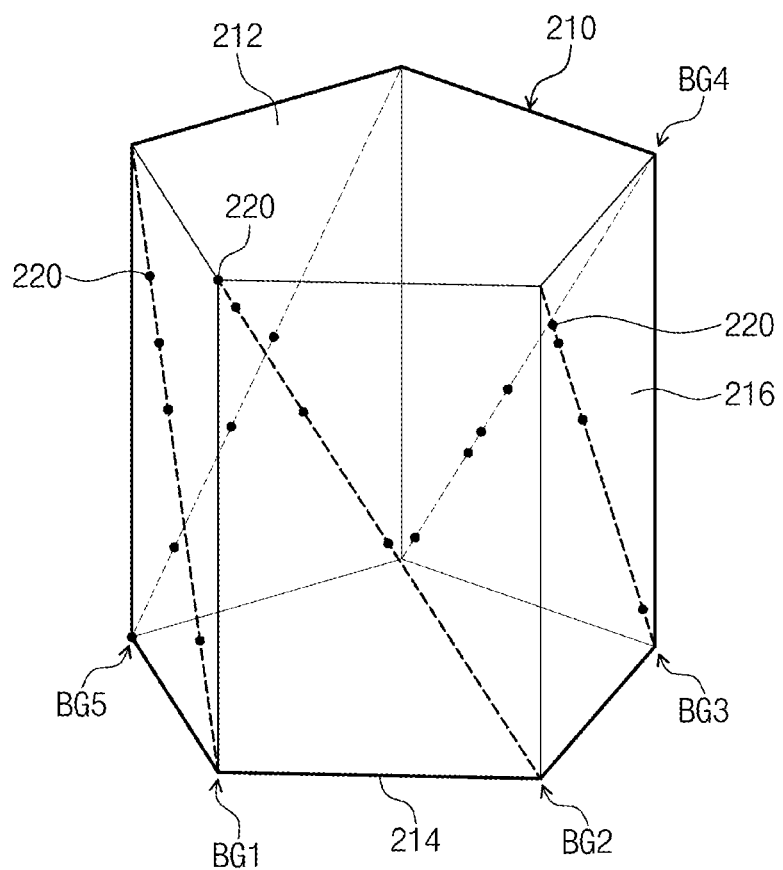
FIG. 2 is a prospective view of a phantom unit according to exemplary embodiments of the inventive concept.
Figure 3:
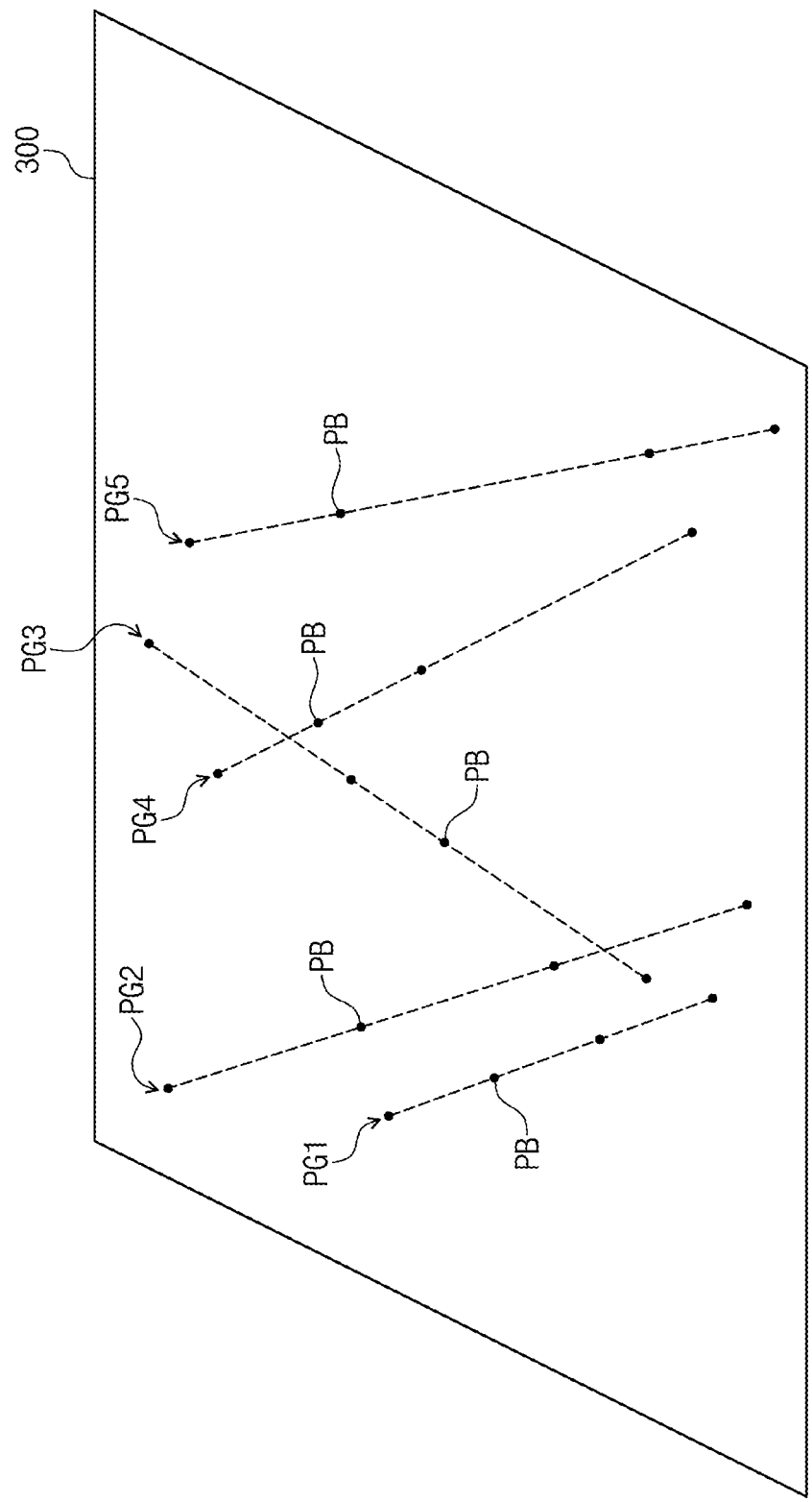
FIG. 3 is a conceptual view of a projection image according to exemplary embodiments of the inventive concept.

FIG. 1 is a block diagram of a calibration system of a three-dimensional imaging equipment. FIG. 2 is a prospective view of a phantom unit according to exemplary embodiments of the inventive concept. FIG. 3 is a conceptual view of a projection image according to exemplary embodiments of the inventive concept.

Referring to FIG. 1, a calibration system 10 of a three-dimensional imaging equipment may be provided which includes a source unit 100, a phantom unit 200, a detector unit 300, and a control unit 400. The source unit 100 may be controlled, by the control unit 400, to emit a radiation 110 towards the phantom unit 200. For example, the radiation 110 may be an x-ray.

Referring to FIG. 2, the phantom unit 200 may include a body 210 and beads 220 disposed on a surface of the body 210. In exemplary embodiments, the body 210 may have an n-prism shape. At this point, n may be an integer of 3 or larger. The body 210 to be described below may have a pentagonal prism shape. Each of a top surface 212 and a bottom surface 214 of the body 210 may be a pentagon. The top surface 212 and the bottom surface 214 may vertically and completely overlap each other. The body 210 may include a material for less absorbing the radiation 110 than the beads 220 do. For example, the body 210 may include a plastic.

The beads may be provided on side surfaces 216 of the body 210. The beads 220 may include a material having a higher radiation absorbance than the body 210. For example, the beads 220 may include a transition metal (e.g. iron (Fe), Nickel (Ni), copper (Cu), tantalum (Ta), tungsten (W), gold (Au)), a post-transition metal (e.g. lead (Pb), thallium metal (Ti)), or an alloy thereof. Since having different radiation absorbances, the body 210 and the beads 220 may be distinguished from each other on an image projected on the detector unit 300.

At least four beads 220 may be provided to each of the side surfaces 216. Hereinafter, a description will be provided about the phantom unit 200 including the four beads 220 provided to each of the side surfaces 216. The four beads 220 may be arranged in a line. For example, the beads 220 may be arranged in a straight line direction from a first vertex of each of the side surfaces 216 towards a second vertex facing the first vertex in a diagonal direction. A dotted line provided to each side surfaces 216 is an imaginary line illustrated to show that the four beads 220 are arranged in a line.

The four beads 220 provided to each of the side surfaces 216 may be defined as a bead group. First to fifth bead groups BG1 to BG5 may be respectively provided on the side surfaces 216. Beads 220 of one (e.g. the first bead group BG1) of the first to fifth bead groups BG1 to BG5 may be disposed to have different 'segment ratios' and different 'cross ratios' from beads 220 of the remaining bead groups (e.g. the second to fifth bead groups BG2 to BG5). In other words, an arrangement pattern of the beads 220 of one (e.g. the first bead group BG1) of the first to fifth bead groups BG1 to BG5 may be different from that of the beads 220 of each of the remaining bead groups (e.g. the second to fifth bead groups BG2 to BG5). For example, an arrangement interval of the beads 220 of the first bead group BG1 may be different from that of the beads 220 of each of the second to fifth bead groups BG2 to BG5. The segment ratios and cross ratios will be described in detail. In the specification, the phantom unit 200 may be called as a calibration device of the three-dimensional imaging equipment.

Referring to FIGS. 1 and 3, the detector unit 300 may receive the radiation 110 penetrating the phantom unit 200 to generate a projection image. The projection image may include projection beads PB formed by the beads 220 that are projected on the detector unit 300. The illustrated projection image is exemplary, and thus should not be restrictively interpreted. The source unit 100 and detector unit 300 may revolve around the phantom unit 200 to generate a plurality of projection images.

The control unit 400 may group the projection beads PB into a first projection group PG1 to a fifth projection group PG5. The projection beads PB of each of the first to fifth projection groups PG1 to PG5 may be arranged in a line. Dotted lines illustrated on the detector unit 300 are imaginary lines illustrated for showing that the projection beads PB of each of the first to fifth projection groups PG1 to PG5 are arranged in a line. The control unit 400 may respectively map the first to fifth projection groups PG1 to PG5 to the first to fifth bead groups BG1 to BG5. For example, when the third bead group BG3 is projected on the detector unit 300 to form the first projection group PG1, the control unit 400 may map the first projection group PG1 to the third bead group BG3. The above-described mapping process will be described in detail below.

The control unit 400 may generate projection matrix (PM) data on the basis of mapping information between the first to fifth projection groups PG1 to PG5 and the first to fifth bead groups BG1 to BG5. The projection matrix may represent a relationship between a projection object and a projection image of the projection object. The projection image may be recovered (inversely projected) as a three-dimensional image by the projection matrix. The projection matrix will be described in detail.

Typically, a plurality of beads may be projected to an identical position on a detector unit. In other words, a plurality of beads may be detected as overlapping on the projection image. Accordingly, it may be difficult to obtain an accurate projection matrix.

The beads 220 according to an embodiment of the inventive concept may be respectively projected at different positions on the detector unit 300. Accordingly, the beads 220 may be separately recognized on the detector unit 300 from each other, and an accurate projection matrix may be acquired.

Figure 4:
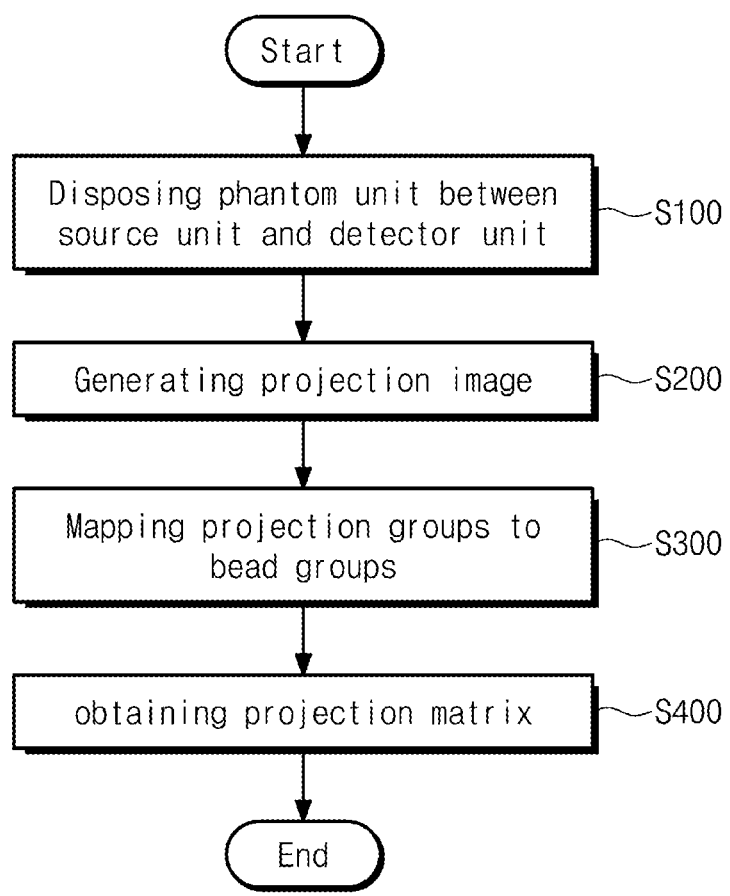
FIG. 4 is a flowchart for explaining a calibration method of a three-dimensional imaging equipment according to exemplary embodiments of the inventive concept.
Figure 5:
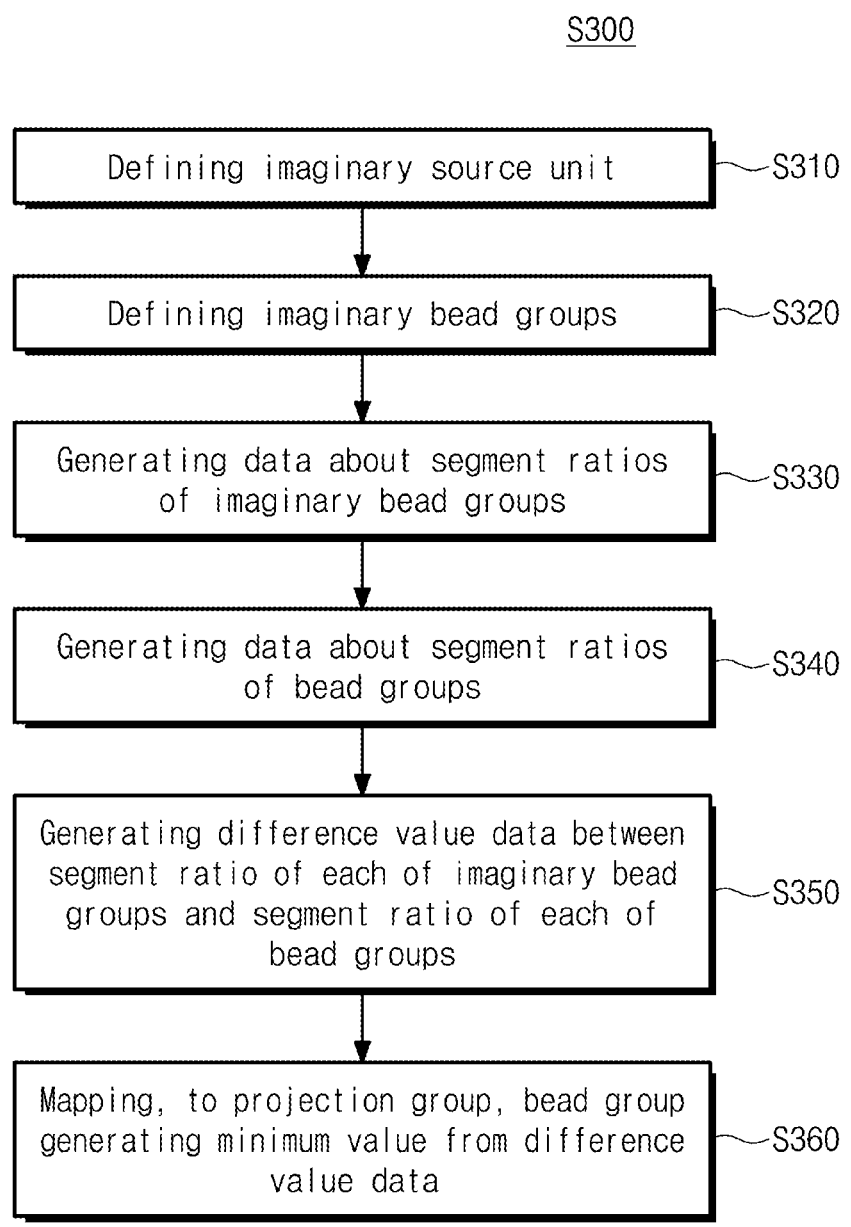
FIG. 5 is a flowchart for explaining a method for mapping bead groups to projection groups by using a segment ratio according to exemplary embodiments of the inventive concept.

FIG. 4 is a flowchart for explaining a calibration method of the three-dimensional imaging equipment according to exemplary embodiments of the inventive concept. FIG. 5 is a flowchart for explaining a method for mapping bead groups to projection groups by using segment ratios according to exemplary embodiments of the inventive concept. FIGS. 6 to 9 are conceptual views for explaining the mapping process of FIG. 5. For clearness of explanation, FIGS. 5 to 9 illustrate only the third projection group PG3 from among the first to fifth projection groups PG1 to PG5 of FIG. 3.

Referring to FIGS. 1, 3, and 4, the phantom unit 200 may be disposed between the source unit 100 and the detector unit 300 (operation S100). The phantom unit 200 may include the first to fifth bead groups BG1 to BG5. Each of the first to fifth bead groups BG1 to BG5 may include four beads 220. The radiation emitted from the source unit 100 may penetrate the phantom unit 200 to reach the detector unit 300. The detector unit 300 may generate data about an incident position of the radiation 110 and provide the data to the control unit 400.

The control unit 400 may generate the projection image on the basis of the data about the incident position of the radiation 110 (operation S200). The projection image may include the projection beads PB formed by the beads 220 that are projected on the detector unit 300.

The control unit 400 may group the projection beads PB and define the first to fifth projection groups PG1 to PG5. Then, the control unit 400 may map the first to fifth projection groups PG1 to PG5 to the first to fifth bead groups BG1 to BG5 (operation S300). Hereinafter, the mapping method of the projection groups and the bead groups will be described in detail.

Figure 6:
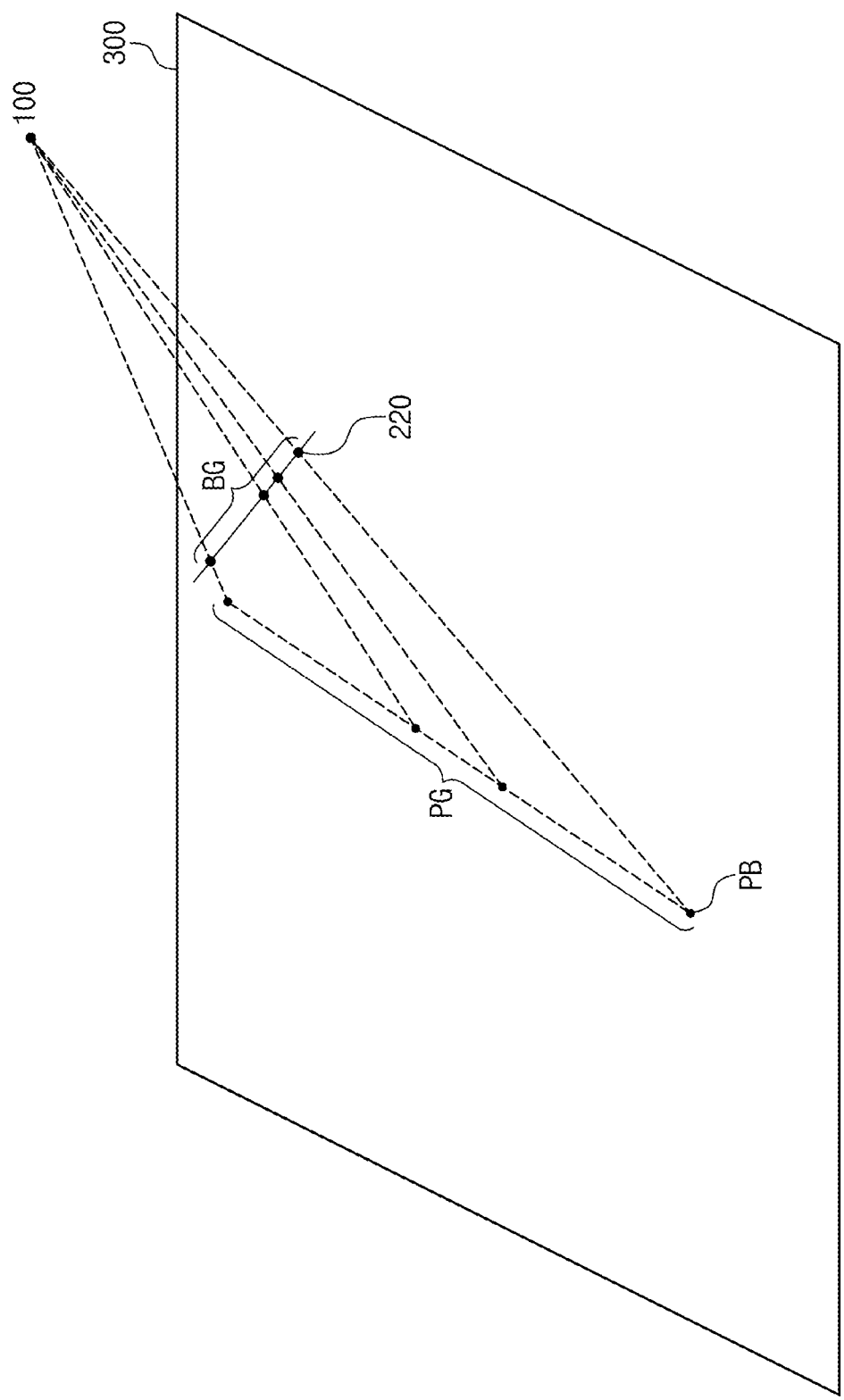
FIGS. 6 to 9 are conceptual views for explaining the mapping process of FIG. 5.

Referring to FIG. 6, provided are the source unit 100, the detector unit 300, the bead group BG disposed between the source unit 100 and the detector unit 300, and the projection group PG formed by the bead group BG that is projected on the detector unit 300. The bead group BG may include four beads 220 arranged in a line. The projection group PG may include four projection beads PB arranged in a line.

Figure 7:
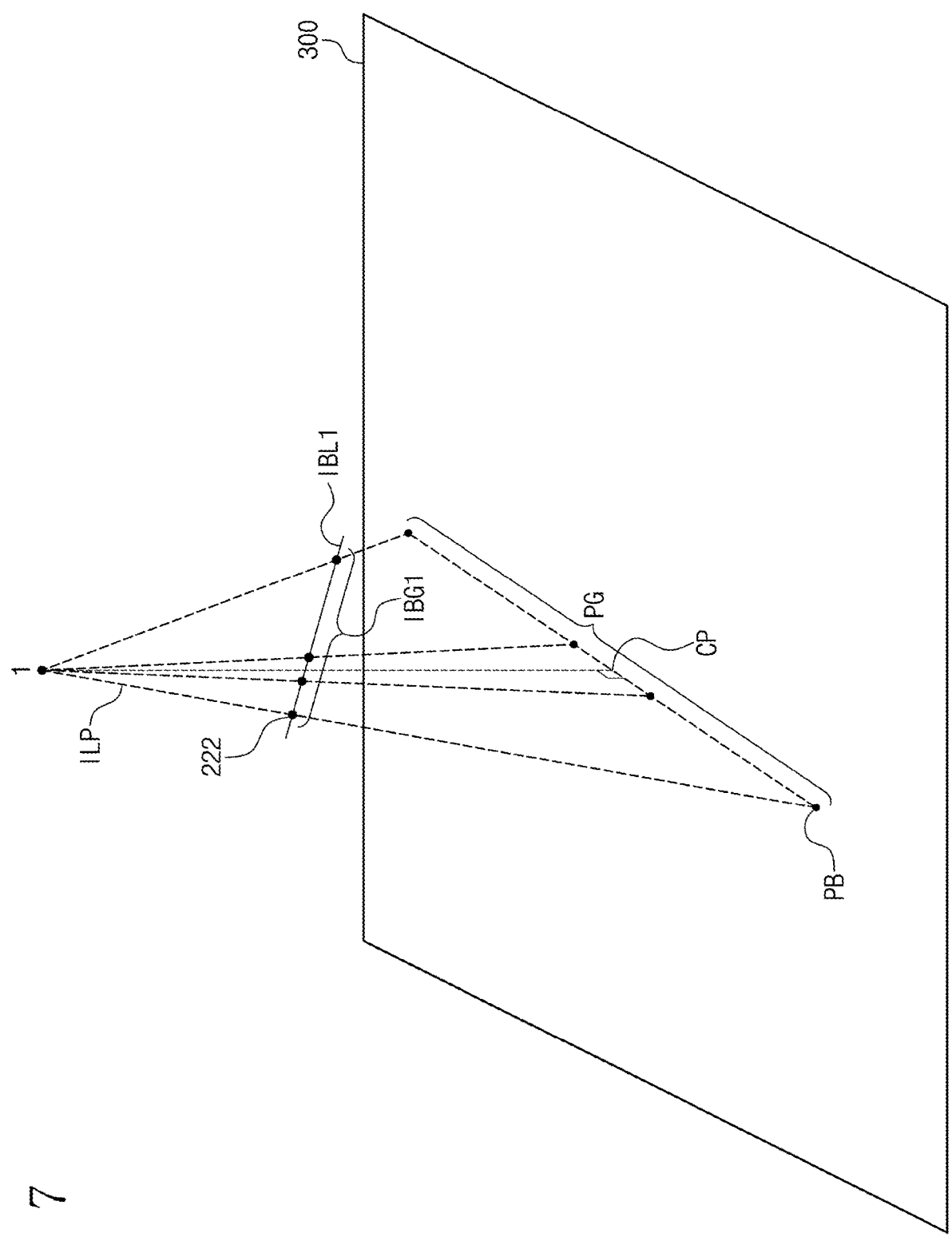

Referring to FIGS. 5 and 7, an imaginary source unit 1 may be provided (operation S310). The imaginary source unit 1 may emit an imaginary radiation traveling an imaginary light path ILP. The imaginary source unit 1 may be separated in a direction perpendicular to the top surface of the detector unit 300 from a center point CP between a pair of projection beads PB, which are separated farthest from each other, from among the projection beads PB. Distances between the imaginary source unit 1 and the pair of projection beads PB may be identical to each other.

A first imaginary bead group IBG1 for generating the projection group PG may be provided by the control unit 400 (operation S320). The first imaginary bead group IBG1 may be disposed between the imaginary source unit 1 and the projection beads PB. The imaginary radiation penetrating the first imaginary bead group IBG1 may form the projection group PG on the detector unit 300. The first imaginary bead group IBG1 may include four imaginary beads 222. Hereinafter, a method for forming the first imaginary bead group IBG1 will be described in detail.

The imaginary source unit 1 and each of the projection beads PB may be connected with straight lines and provide imaginary light paths ILP. Then, a first imaginary bead line IBL1, which is a straight line crossing the imaginary light paths ILP, may be provided. The imaginary light paths ILP cross the first imaginary bead line IBL1 to form four cross points. The first imaginary bead group IBG1 may include four imaginary beads 222 respectively disposed at the cross points.

Figure 8:
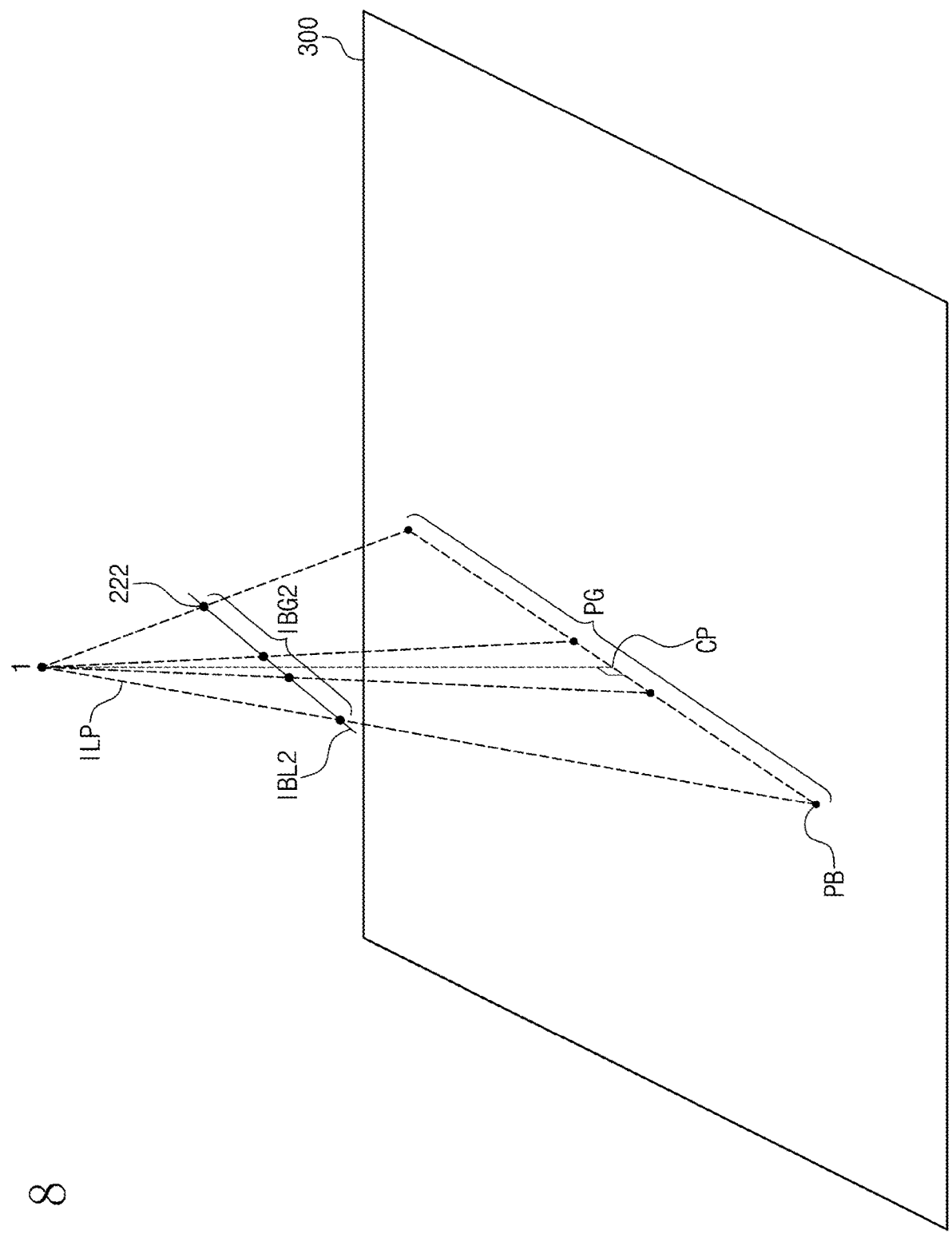

Referring to FIG. 8, a second imaginary bead line IBL2 may be provided which crosses the imaginary light paths ILP but is different from the first imaginary bead line IBL1. For example, the first imaginary bead line IBL1 and the second imaginary bead line IBL2 are on the same plane, but an inclination of the first imaginary bead line IBL1 may be different from that of the second imaginary bead line IBL2 with respect to the top surface of the detector unit 300. The imaginary light paths ILP cross the second imaginary bead line IBL2 to form four cross points. The second imaginary bead group IBG2 may include four imaginary beads 222 respectively disposed at the cross points.

Figure 9:
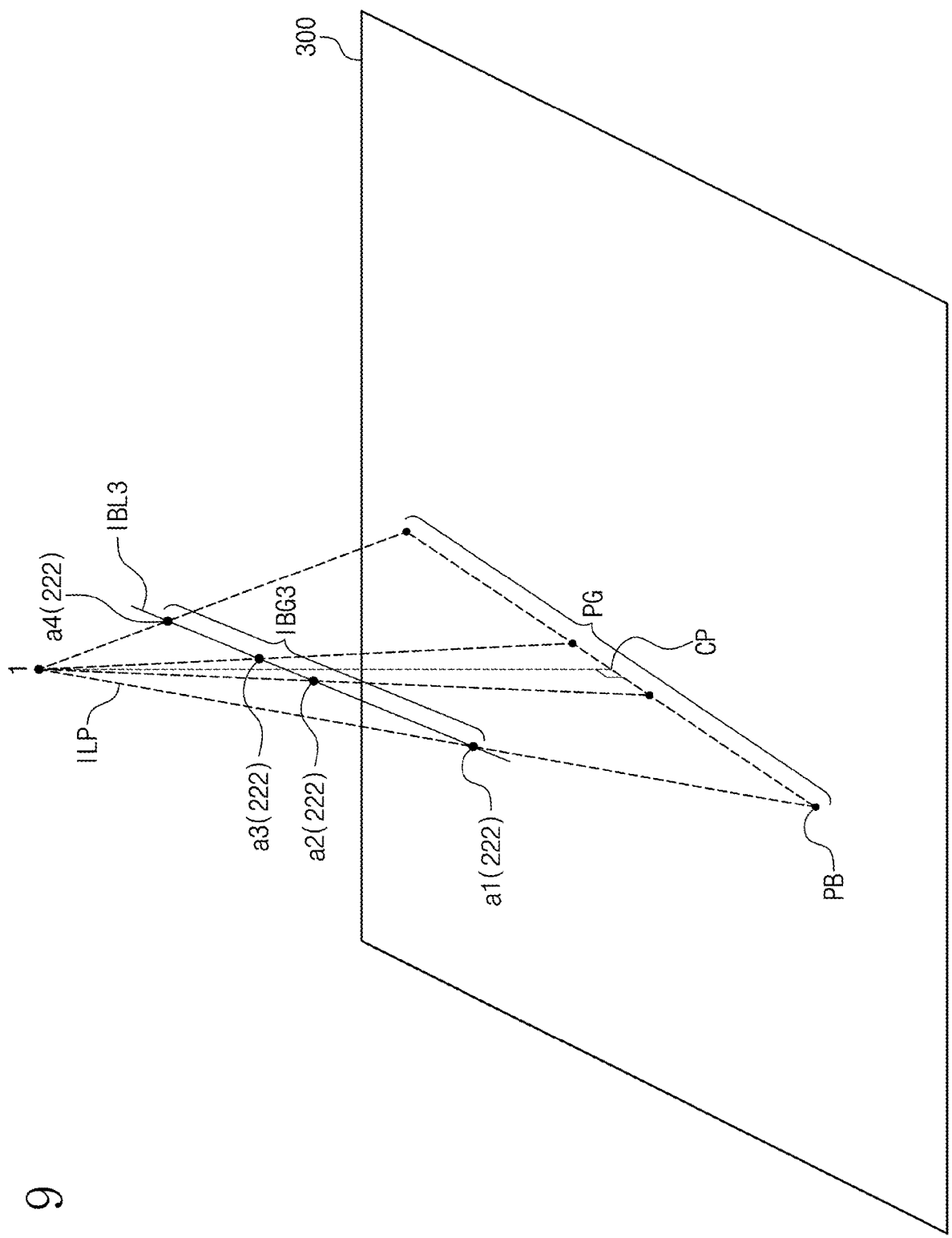

Referring to FIG. 9, a third imaginary bead line IBL3 may be defined which crosses the imaginary light paths ILP but is different from the first and second imaginary bead lines IBL1 and IBL2. For example, the first imaginary bead line IBL1, the second imaginary bead line IBL2, and the third imaginary bead line IBL3 are on the same plane, but the inclinations of the first and second imaginary bead lines IBL1 and IBL2 may be different from that of the third imaginary bead line IBL3 with respect to the top surface of the detector unit 300. The imaginary light paths ILP cross the third virtual bead line IBL3 to form four cross points. The third imaginary bead groups IBG3 may include first to fourth imaginary beads a1, a2, a3, and a4 respectively disposed at the cross points.

Similar to the above-described scheme, additional imaginary bead groups, besides the first to third imaginary bead group IBG1, IBG2, and IBG3, may be provided. Accordingly, data about imaginary bead groups may be generated, the image groups being different from each other and forming the projection group PG. The data about the imaginary bead groups may include position information about each of the imaginary beads included in the imaginary bead groups.

The control unit 400 may generate data about a segment ratio of each of the imaginary bead groups on the basis of the data about the imaginary bead groups (operation S330). Referring to FIG. 9, the segment ratio will be described for the third imaginary bead group IBG3 including the first to fourth beads a1 to a4.

The segment ratio of the first to fourth imaginary beads a1 to a4 may be a ratio of a distance between two imaginary beads (e.g. the first imaginary bead a1 and the fourth imaginary bead a4) from among the first to fourth imaginary beads a1 to a4, to a distance between other two imaginary beads (e.g. the first imaginary bead a1 and the second imaginary bead a2) different therefrom.

The segment ratio may be expressed as Equation (1).

$$\text{segment ratio} = \frac{\overline{a1a2}}{\overline{a1a4}} \quad (1)$$

where $\overline{a1a2}$ denotes a distance between the first and second imaginary beads, and $\overline{a1a4}$ denotes a distance between the first and fourth imaginary beads.

A first segment ratio and a second segment ratio independent of each other may be generated from the first to fourth imaginary beads a1 to a4. For example, the first segment ratio and the second segment ratio may be expressed as the following Equation (2).

$$1st \text{ segment ratio} = \frac{\overline{a1a2}}{\overline{a1a4}} \quad (2)$$

$$2nd \text{ segment ratio} = \frac{\overline{a1a3}}{\overline{a1a4}}$$

where $\overline{a1a2}$ denotes a distance between the first and second imaginary beads, $\overline{a1a4}$ denotes a distance between the first and fourth imaginary beads, and $\overline{a1a3}$ denotes a distance between the first and third imaginary beads.

In other words, the data about each of the segment ratios of the imaginary bead groups may include the first segment ratio and the second segment ratio of each of the imaginary bead groups. The control unit 400 may generate data about a segment ratio of each of the first to fifth bead groups BG1 to BG5 described in relation to FIG. 3 (operation S340). The data about the segment ratio of each of the first to fifth bead groups BG1 to BG5 may include a third segment ratio and a fourth segment ratio independent of each other. The third and fourth segment ratios may be generated by the substantially same scheme as that of the first and second segment ratios. The third segment ratio may correspond to the first segment ratio, and the fourth segment ratio may correspond to the second segment ratio. The control unit 400 may generate difference value data between data about the segment ratios of the imaginary bead groups and data about the segment ratios of the bead groups (operation S350). The difference value data may include a first difference value between the first segment ratio of each of the imaginary bead groups and the third segment ratio of each of the bead groups, and a second difference value between the second segment ratio of each of the imaginary bead groups and the fourth segment ratio of each of the bead groups.

The control unit 400 may select one bead group generating a minimum first difference value and a minimum second difference value from among the first to fifth bead groups BG1 to BG5. The minimum first difference value and the minimum second difference value may be generated from the same bead group. The control unit 400 may determine that the selected bead group corresponds to the projection group (operation S360).

The control unit 400 may generate data about the projection matrix PM by using data about positions of the beads 220 and the projection beads PB corresponding to each other (operation S400). The projection matrix PM may include information about how an inspection object (e.g. the bead) that is a three-dimensional object is projected on a two-dimensional projection image. The projection matrix PM is a 3×4 matrix and may be acquired from the following Equation (3).

$$u(P_{31}x+P_{32}y+P_{33}z+P_{34})=P_{11}x+P_{12}y+P_{13}z+P_{14}$$

$$v(P_{31}x+P_{32}y+P_{33}z+P_{34})=P_{21}x+P_{22}y+P_{23}z+P_{24} \quad (3)$$

where $P_{nm}$ (where n is 1, 2 or 3, m is 1, 2, 3 or 4) denotes an element of the projection matrix, (x, y, z) denotes three-dimensional position coordinates of the bead, and (u, v) denotes two-dimensional coordinates on the projection image of the projection bead.

The three-dimensional coordinates (x, y, z) of the bead is predetermined values, and the two-dimensional coordinates of the projection bead is measured values. Accordingly, after the x, y, z, u, and v are substituted, when a singular value decomposition scheme is applied, a solution of the projection matrix may be acquired. At this point, (x, y, z) and (u, v) may be respectively the three-dimensional position coordinates of the bead and the two-dimensional position coordinates on the projection image of the projection bead corresponding to the bead. The projection matrix may inversely project the two-dimensional projection image onto the three dimension in the three-dimensional imaging equipment to be used as information for recovering a three-dimensional image. The three-dimensional image may be acquired from the following Equation (4).

$$PM \begin{pmatrix} x \\ y \\ z \\ 1 \end{pmatrix} = -y_C \begin{pmatrix} u \\ v \\ 1 \end{pmatrix} \quad (4)$$

where PM denotes the projection matrix and $y_c$ denotes a scale factor.

The acquired projection matrix PM and already known x, y, and z values are substituted to Equation (4) to obtain u and v that are two-dimensional coordinates on the projection image, and yc that is a scale factor. Accordingly, when the projection matrix PM is acquired, the two-dimensional projection image may be inversely projected onto the three dimension. Accordingly, the three-dimensional image may be acquired.

Typically, as the three-dimensional imaging equipment is used, an arrangement state of the equipment may be changed. Accordingly, values of the projection matrix PM are changed and quality of the image may be lowered. In order to obtain a precise image, the values of the projection matrix PM are required to be calibrated. In a typical calibration method of a three-dimensional equipment, beads may be recognized as overlapping and thus it may be difficult to obtain an accurate solution of the projection matrix PM. In addition, since a typical calibration method of the three-dimensional imaging equipment is required to undergo a complex calculation process, a long calibration time may be required.

The beads according to the inventive concept may be easily separately recognized on the projection image, and mapping accuracy between the projection group and the bead group may be improved and thus a precise solution of the projection matrix PM may be acquired. In addition, since the projection matrix PM is acquired by performing a simple calculation, the calibration time may be shortened.

Figure 10:
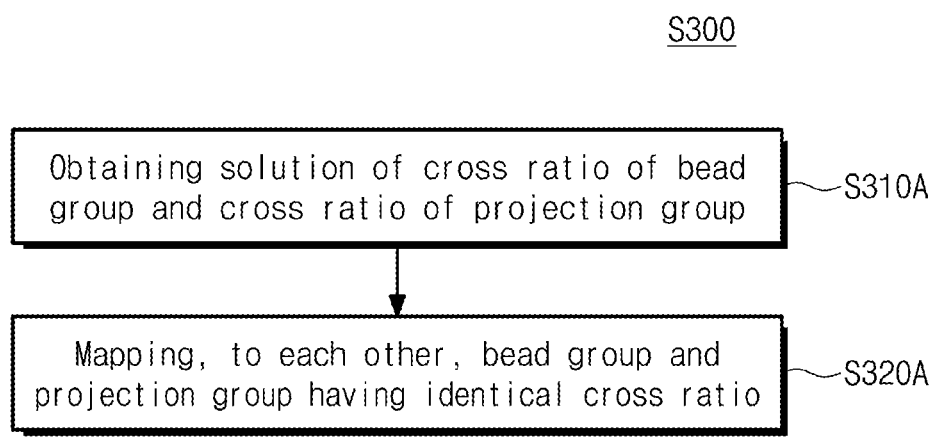
FIG. 10 is a flowchart for explaining a method for mapping bead groups to projection groups by using a cross ratio according to exemplary embodiments of the inventive concept.
Figure 11:
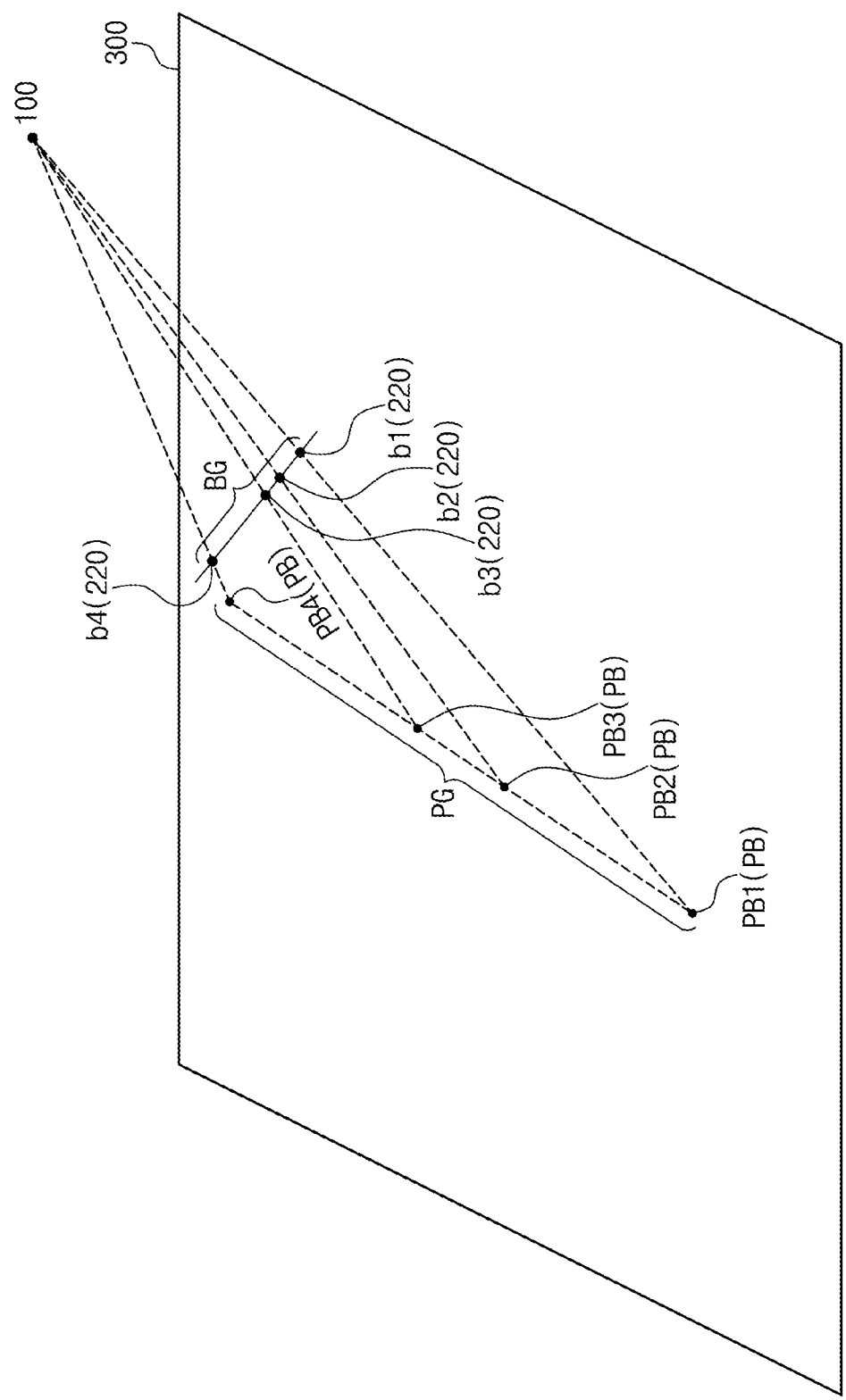
FIG. 11 is a conceptual view for explaining the mapping process of FIG. 10.

FIG. 10 is a flowchart for explaining a method for mapping bead groups to projection groups by using a cross ratio according to exemplary embodiments of the inventive concept. FIG. 11 is a conceptual view for explaining the mapping process of FIG. 10. For conciseness of explanation, contents substantially identical to those described in relation to FIGS. 4 to 9 may not be described.

Referring to FIGS. 10 and 11, provided are the source unit 100, the detector unit 300, the bead group BG disposed between the source unit 100 and the detector unit 300, and the projection group PG formed by the bead group BG that is projected on the detector unit 300. The bead group BG may include first to fourth beads b1, b2, b3, and b4 arranged in a line. The projection group PG may be that the bead group BG is projected onto the detector unit 300. The projection group PG may include first to fourth projection beads PB1, PB2, PB3, and PB4 arranged in a line. The detector unit 300 may generate data about positions on projection images of the first to fourth projection beads PB1 to PB4 and provide the data to the control unit 400.

The control unit 400 may generate cross ratio data of the bead group BG and cross ratio data of the projection group PG (operation S310A). The cross ratio of the bead group BG and the cross ratio of the projection group PG may be expressed as the following Equations (5).

$$\text{cross ratio of bead group} = \frac{\overline{b1b3}}{\overline{b2b3}} \cdot \frac{\overline{b2b4}}{\overline{b1b4}} \quad (5)$$

$$\text{cross ratio of projection group} = \frac{\overline{PB1PB3}}{\overline{PB2PB3}} \cdot \frac{\overline{PB2PB4}}{\overline{PB1PB4}}$$

where $\overline{b1b3}$ denotes a distance between the first and third beads, $\overline{b2b4}$ denotes a distance between the second and fourth beads, $\overline{b2b3}$ denotes a distance between the second and third beads, and $\overline{b1b4}$ denotes a distance between the first and fourth beads, and where $\overline{PB1PB3}$ denotes a distance between the first and third projection beads, $\overline{PB2PB4}$ denotes a distance between the second and fourth projection beads, $\overline{PB2PB3}$ denotes a distance between the second and third projection beads, and $\overline{PB1PB4}$ denotes a distance between the first and fourth projection beads.

Cross ratios of cross points of a first straight line crossing a plurality of straight lines extending from one point towards different directions are identical to cross ratios of cross points of a second straight line crossing the straight lines are the same. Accordingly, the cross ratio of the bead group BG and the cross ratio of the projection group PG are identical to each other. The control unit 400 may map the projection group PG to the bead group BG having the same cross ratio as that of the projection group PG (operation S320A).

The beads according to the inventive concept may be easily recognized as separated on the projection image, and mapping accuracy between the projection group and the bead group may be improved and thus a precise solution of the projection matrix PM may be acquired.

Figure 12:
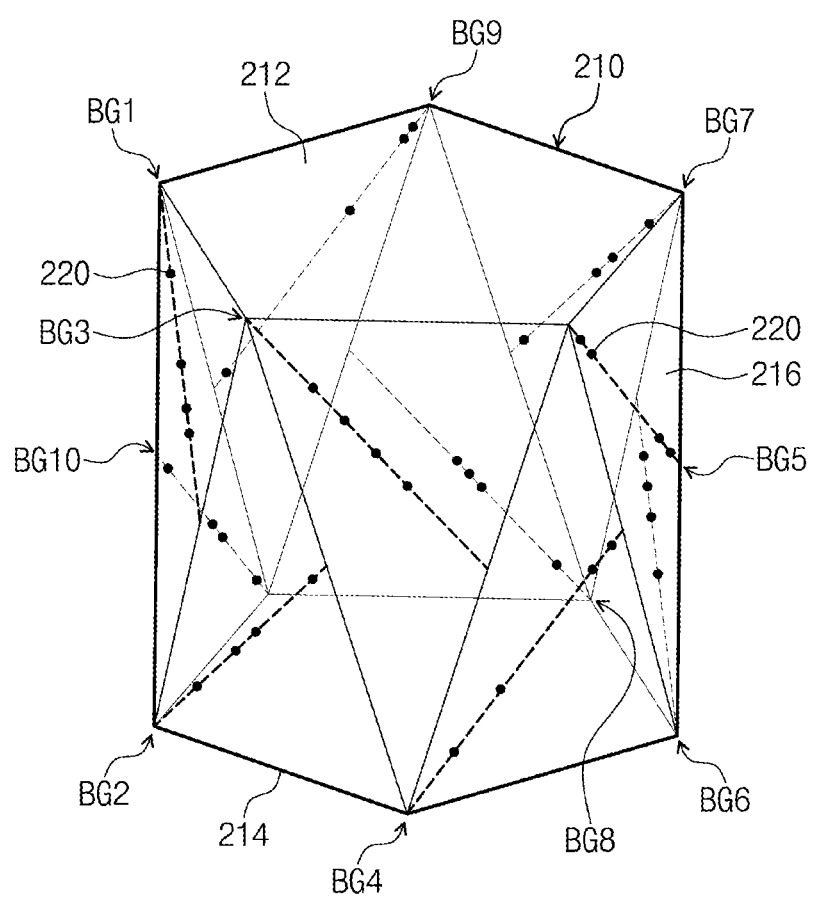
FIG. 12 is a prospective view of a phantom according to exemplary embodiments of the inventive concept.

FIG. 12 is a prospective view of a phantom according to exemplary embodiments of the inventive concept. For conciseness of explanation, contents substantially identical to those described in relation to FIG. 2 may not be described.

Referring to FIG. 12, the phantom unit 200A having the body 210 of a polyhedron shape may be provided. Each of the top surface 212 and the bottom surface 214 of the body 210 may be a pentagon. The top surface 212 and the bottom surface 214 may face each other out of line. For example, the top surface 212 and the bottom surface 214 may not vertically and completely overlap each other.

Side surfaces 216 of the body 210 may be triangular. Each of the side surfaces 216 may be obtained by connecting one vertex of the top surface 212 and a pair of vertexes of the bottom surface 214 just adjacent to the one vertex or by connecting one vertex of the bottom surface 214 and a pair of vertexes of the top surface 212 just adjacent to the one vertex.

As the phantom unit 200 having been described in relation to FIG. 2, at least four beads 220 may be provided to each of the side surfaces 216. The four beads 220 may be arranged in a line. For example the beads 220 may be arranged in a straight line direction from one vertex of the side surfaces 216 towards the center of side facing the one vertex. A dotted line provided to each side surfaces 216 is an imaginary line illustrated to show that the four beads 220 are arranged in a line.

The four beads 220 provided to each of the side surfaces 216 may be defined as a bead group. First to tenth bead groups BG1 to BG10 may be respectively provided on the side surfaces 216. Beads 220 of one bead group (e.g. the first bead group BG1) from among the first to tenth bead groups BG1 to BG10 may be disposed to have different 'segment ratios' and different 'cross ratios' from beads 220 of the remaining bead groups (e.g. the second to tenth bead groups BG2 to BG10). For example, an arrangement interval of the beads 220 of the first bead group BG1 may be different from that of the beads 220 of each of the second to tenth bead groups BG2 to BG10.

Typically, a plurality of beads may be projected to an identical position on a detector unit. In other words, the plurality of beads may be detected as overlapping on the projection image. Accordingly, it may be difficult to obtain an accurate projection matrix.

The beads 220 according to the inventive concept may be respectively projected at different positions on the detector unit 300. Accordingly, the beads 220 may be recognized, on the detector unit 300, as separated from each other, and an accurate projection matrix may be acquired. A process for generating the projection matrix may be substantially identical to the above-described.

According to embodiments of the inventive concept, a precise solution of a projection matrix may be acquired.

According to embodiments of the inventive concept, the beads may be separately projected on the detector unit.

However, the effects of the inventive concept are not limited to the above-described disclosure.

The above-described description about the embodiments of the inventive concept provides examples for explaining the inventive concept. Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A calibration device for three-dimensional imaging equipment comprising:
    a first bead group comprising first beads arranged in a first pattern; and
    a second bead group comprising second beads arranged in a second pattern different from the first pattern,
    wherein the first and second bead groups have different cross ratios or different segment ratios from each other, the first beads are arranged in a line, and the second beads are arranged in a line.

2. The calibration device of claim 1, further comprising:
    a body having a polyhedron shape,
    wherein the body comprises first and second side surfaces having a rectangular shape, and the first and second bead groups are respectively provided onto the first and second side surfaces.

3. The calibration device of claim 2, wherein the first beads are arranged in a first straight line direction from a first vertex of the first side surface towards a second vertex facing in a first diagonal direction, and
    the second beads are arranged in a second straight line direction from a third vertex of the second side surface towards a fourth vertex facing in a second diagonal direction.

4. The calibration device of claim 1, wherein the first beads are at least four, and the second beads are at least four.

5. The calibration device of claim 1, wherein arrangement intervals between the first beads are different from those between the second beads.

6. The calibration device of claim 1, further comprising:
    a body having a polyhedron shape,
    wherein the body comprises first and second side surfaces different from each other, and the first and second bead groups are provided onto the first and second side surfaces.

7. The calibration device of claim 6, wherein each of the first and second side surfaces is triangular.

8. The calibration device of claim 7, wherein the first beads are arranged in a first straight line direction from a first vertex of the first side surface towards a center of a side facing the first vertex, and
    the second beads are arranged in a second straight line direction from a second vertex of the second side surface towards a center of a side facing the second vertex.

* * * * *